US009066086B2

(12) United States Patent
Angot et al.

(10) Patent No.: US 9,066,086 B2
(45) Date of Patent: Jun. 23, 2015

(54) METHODS FOR GENERATING STEREOSCOPIC VIEWS FROM MONOSCOPIC ENDOSCOPE IMAGES AND SYSTEMS USING THE SAME (75) Inventors: Ludovic Angot, Hsinchu (TW); Kai-Che Liu, Kaohsiung (TW); Wei-Jia Huang, Nantou County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 183 days.

(21) Appl. No.: 13/991,380

(22) PCT Filed: Dec. 8, 2010

(86) PCT No.: PCT/CN2010/079571
§ 371 (c)(1),
(2), (4) Date: Jun. 3, 2013

(87) PCT Pub. No.: WO2012/075631
PCT Pub. Date: Jun. 14, 2012

(65) Prior Publication Data
US 2013/0259315 A1    Oct. 3, 2013

(51) Int. Cl.
*G06K 9/00* (2006.01)
*H04N 13/02* (2006.01)
*G06T 7/00* (2006.01)

(52) U.S. Cl.
CPC ............ *H04N 13/026* (2013.01); *G06T 7/0081* (2013.01); *G06T 7/0083* (2013.01); *G06T 2207/10028* (2013.01); *G06T 2207/10068* (2013.01); *G06T 2207/20061* (2013.01); *H04N 2213/003* (2013.01)

(58) Field of Classification Search
None
See application file for complete search history.

(56) References Cited

U.S. PATENT DOCUMENTS

| 4,271,829 A | 6/1981 | Heckele |
| 5,575,754 A | 11/1996 | Konomura |
| 5,669,871 A | 9/1997 | Sakiyama |

(Continued)

FOREIGN PATENT DOCUMENTS

| EP | 1444953 | 8/2004 |
| JP | 2005034654 | 2/2005 |

(Continued)

OTHER PUBLICATIONS

Angot et al (A 2D to 3D video and image conversion technique based on bilateral filter, Proceedings of the SPE, vol. 7526, pp. 1-10, SPIE 2010).*

(Continued)

*Primary Examiner* — Amara Abdi
(74) *Attorney, Agent, or Firm* — Muncy, Geissler, Olds & Lowe, P.C.

(57) ABSTRACT

Methods for generating stereoscopic views from monoscopic endoscope images and systems using the same are provided. First, monoscopic images are obtained by capturing images of organs in an operating field via an endoscope. A background depth map of the operating field is obtained for each image. An instrument depth map corresponding to an instrument is obtained for each image, wherein the instrument is inserted in a patient's body cavity. The background depth maps and the instrument depth maps are merged to generate an integrated depth map for each image. Stereoscopic views are generated according to the monoscopic images and the integrated depth maps.

25 Claims, 11 Drawing Sheets

(56) References Cited

U.S. PATENT DOCUMENTS

| | | | |
|---|---|---|---|
| 5,693,003 A | 12/1997 | Wölfelschneider et al. | |
| 6,139,490 A | 10/2000 | Breidenthal et al. | |
| 6,275,335 B1 | 8/2001 | Costales | |
| 6,383,131 B1 | 5/2002 | Yamamoto et al. | |
| 6,503,195 B1 | 1/2003 | Keller et al. | |
| 7,170,677 B1 | 1/2007 | Bendall et al. | |
| 7,275,335 B2 | 10/2007 | Holec et al. | |
| 7,385,708 B2 | 6/2008 | Ackerman et al. | |
| 7,447,537 B1 | 11/2008 | Funda et al. | |
| 7,471,291 B2 | 12/2008 | Kaufman et al. | |
| 7,480,402 B2 * | 1/2009 | Bar-Zohar et al. | 382/131 |
| 7,564,626 B2 | 7/2009 | Bendall et al. | |
| 7,671,888 B2 | 3/2010 | Nogami et al. | |
| 2002/0077544 A1 | 6/2002 | Shahidi | |
| 2002/0107444 A1 | 8/2002 | Adler | |
| 2009/0054764 A1 | 2/2009 | Adler et al. | |
| 2010/0030063 A1 | 2/2010 | Lee et al. | |
| 2010/0079453 A1 * | 4/2010 | Chen et al. | 345/421 |

FOREIGN PATENT DOCUMENTS

| | | | |
|---|---|---|---|
| TW | 201015491 A | 4/2010 | |
| TW | I323425 | 4/2010 | |
| WO | WO 2006/111965 | | 10/2006 |
| WO | WO 2010/035223 A1 | | 4/2010 |
| WO | WO 2010/125481 A1 | | 11/2010 |
| WO | WO 2011/060579 | | 5/2011 |

OTHER PUBLICATIONS

Taiwan Office Action for Taiwan Application No. 099147213 dated Nov. 12, 2013.

L. J. Angot et al., "A 2D to 3D video and image conversion technique based on a bilateral filter," Three-Dimensional Image Processing (3DIP) and Applications. Edited by Baskurt, Atilla M. Proceedings of the SPIE, vol. 7526, article id. 75260D, 10 pp. (2010).

A. F. Durrani et al., "Three-dimensional video imaging for endoscopic surgery," Comput. Biol. Med. vol. 25, No. 2, pp. 237-247, 1995.

M. M. Fenske et al., "A Design of a Liquid Crystal Based Single-Lens Stereo Endoscope," Bioengineering Conference, 2006, Proceedings of the IEEE $32^{nd}$ Annual Northeast, pp. 43-44.

M. E. Levinson et al., "Development of an autostereoscopic monitor and 2D to 3D conversion for medical and surgical uses; requirements, clinical trials, and degree of acceptance," Proc. SPIE3639, Stereoscopic Displays and Virtual Reality Systems VI, pp. 36-43, (May 24, 1999).

* cited by examiner

METHODS FOR GENERATING STEREOSCOPIC VIEWS FROM MONOSCOPIC ENDOSCOPE IMAGES AND SYSTEMS USING THE SAME

BACKGROUND

1. Technical Field

This disclosure relates generally to methods for generating stereoscopic views and systems using the same, and, more particularly to methods for generating stereoscopic views from monoscopic images captured by an endoscope and systems using the same.

2. Description of the Related Art

Minimal invasive surgery (MIS) consists of using an imaging system and instruments of small diameters which can be introduced in small incisions in the body, in order to reduce the sequels of surgical interventions. The imaging system is in most cases a monoscopic endoscope consisting of an optical system, a camera, a sensor or the like and a display system. The monoscopic nature of the imaging system requires surgeons a long and tedious training period prior to operation, because the sensation of depth is absent, contrary to traditional open surgery where stereopsis naturally occurs to the surgeon. There is therefore a need to provide surgeons with depth sensation when performing a MIS operation. However, though stereoscopic endoscopes exist, there is still the need to provide stereoscopic views from monoscopic images.

SUMMARY

Methods for generating stereoscopic views from monoscopic endoscope images and systems using the same are provided.

In an exemplary embodiment of a method for generating stereoscopic views from monoscopic endoscope images, monoscopic images are obtained by capturing, with an endoscope, images of organs in an operating field. A background depth map of the operating field is obtained for each image corresponding to the organs on which the operation is to be performed. An instrument depth map corresponding to the depth of one or more instruments used during the operation is obtained for each image, wherein the one or more instruments are inserted in the patient's body cavity through a small incision. The background depth map and the instrument depth map are then merged to generate an integrated depth map for each image. Stereoscopic views are generated according to the monoscopic images and the corresponding integrated depth maps.

An exemplary embodiment of a system for generating stereoscopic views from monoscopic endoscope images includes a storage unit and a processing unit. The storage unit includes monoscopic images, wherein the monoscopic images captured with an endoscope are images of organs in an operating field. The processing unit calculates, for each monoscopic image, a background depth map of the operating field, and calculates an instrument depth map corresponding to one or more instruments used during the operation, wherein the one or more instruments are inserted in the patient's body cavity through a small incision. The processing unit merges the background depth map and the instrument depth map to generate an integrated depth map for each monoscopic image. The processing unit generates stereoscopic views according to the monoscopic images and the corresponding integrated depth map.

Methods for generating stereoscopic views from monoscopic endoscope images may take the form of a program code embodied in a tangible media. When the program code is loaded into and executed by a machine, the machine becomes an apparatus for practicing the disclosed method.

BRIEF DESCRIPTION OF THE DRAWINGS

The disclosure will be better understood by referring to the following detailed description with reference to the accompanying drawings, wherein.

DETAILED DESCRIPTION

Methods for generating stereoscopic views from monoscopic endoscope images and systems using the same are provided.

Figure 1:
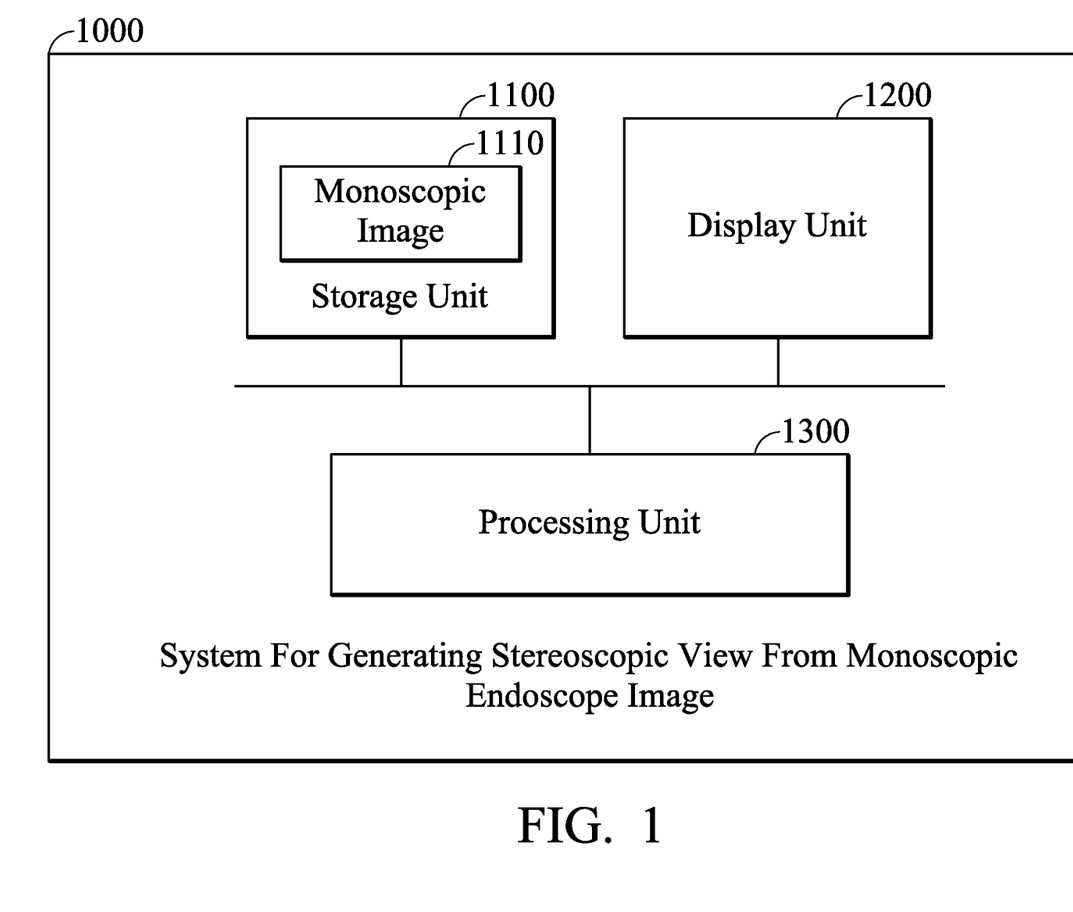
FIG. 1 is a schematic diagram illustrating an exemplary embodiment of a system for generating stereoscopic views from monoscopic endoscope images of the disclosure.

FIG. 1 is a schematic diagram illustrating an exemplary embodiment of a system for generating stereoscopic views from monoscopic endoscope images of the disclosure. The system for generating stereoscopic views from monoscopic endoscope images 1000 can be used in an electronic device, such as a monoscopic endoscope, a computer system, a display device, a receiving device, a playback device, a capturing device, and others.

The system for generating stereoscopic views from monoscopic endoscope images 1000 comprises a storage unit 1100, a display unit 1200, and a processing unit 1300. The storage unit 1100 comprises at least one monoscopic image 1110. It is understood that the monoscopic images 1110 can be captured by an image capture unit (not shown) of an endoscope. The monoscopic images 1110 are obtained by capturing images of organs in an operating field, such as thorax, abdominal cavity, pelvic cavity, pericardial cavity, pleural cavity, and others, via the endoscope. The display unit 1200 can display at least one stereoscopic view generated by the system. It is understood that, in some embodiments, the stereoscopic views may have at least two images, such as a right image and a left image, thereby forming the 3D effect. It is understood that, the display unit 1200 may be an autostereoscopic display, a parallax barrier or lenticular display, a head mount display, or a display with polarized glasses or time multiplexed glasses. The processing unit 1300 performs the method for generating stereoscopic views from monoscopic endoscope images of the disclosure, which will be discussed further in the following paragraphs. It is understood that, in the present disclosure, one or more instruments, such as a grasper can be inserted in the operating filed, and the stereoscopic views will comprise both the instrument and the organs in the operating field.

Figure 2:
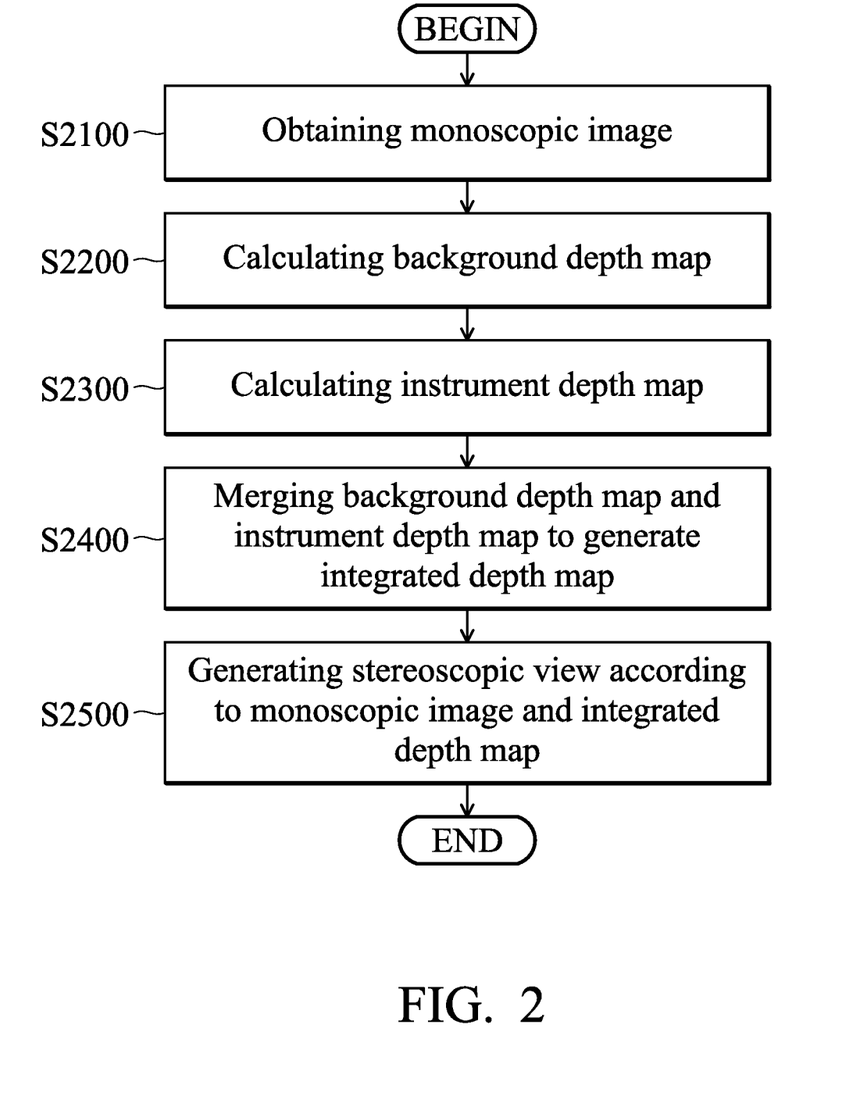
FIG. 2 is a flowchart of an exemplary embodiment of a method for generating stereoscopic views from monoscopic endoscope images of the disclosure.

FIG. 2 is a flowchart of an exemplary embodiment of a method for generating stereoscopic views from monoscopic endoscope images according to the present disclosure.

Figure 3:
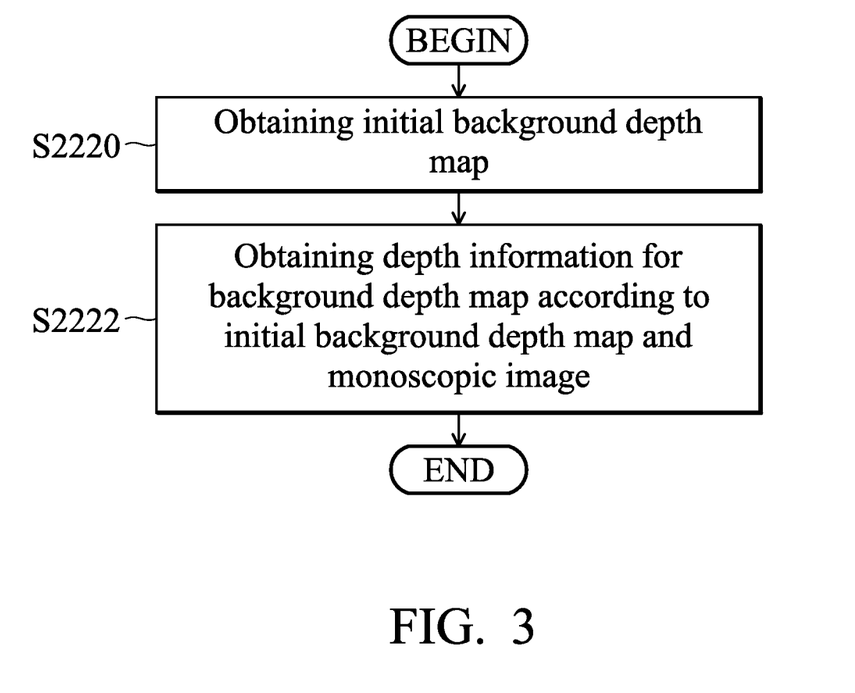
FIG. 3 is a flowchart of an exemplary embodiment of a method for calculating a background depth map of the disclosure.
Figure 5A:
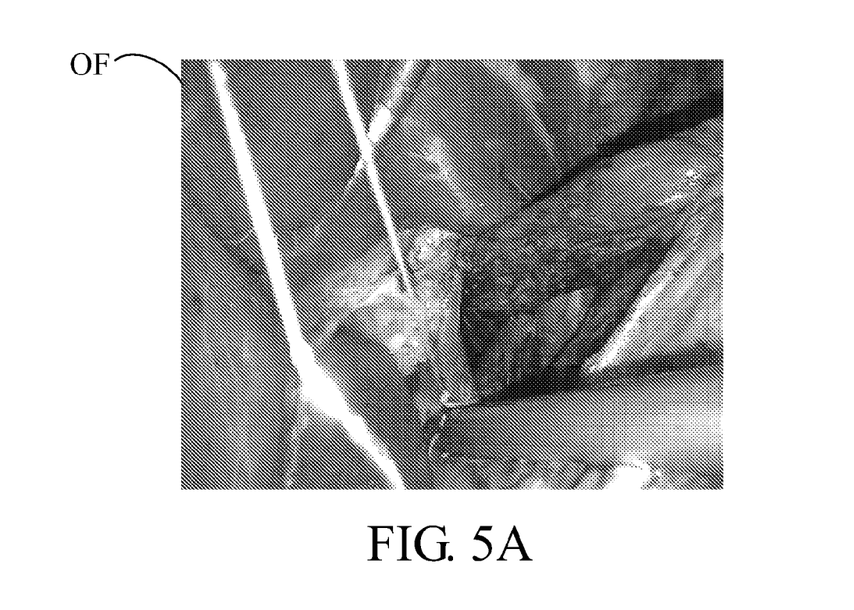
FIGS. 5A~5C show an example of an initial background depth map obtained by a 2D to 3D conversion.
Figure 5B:
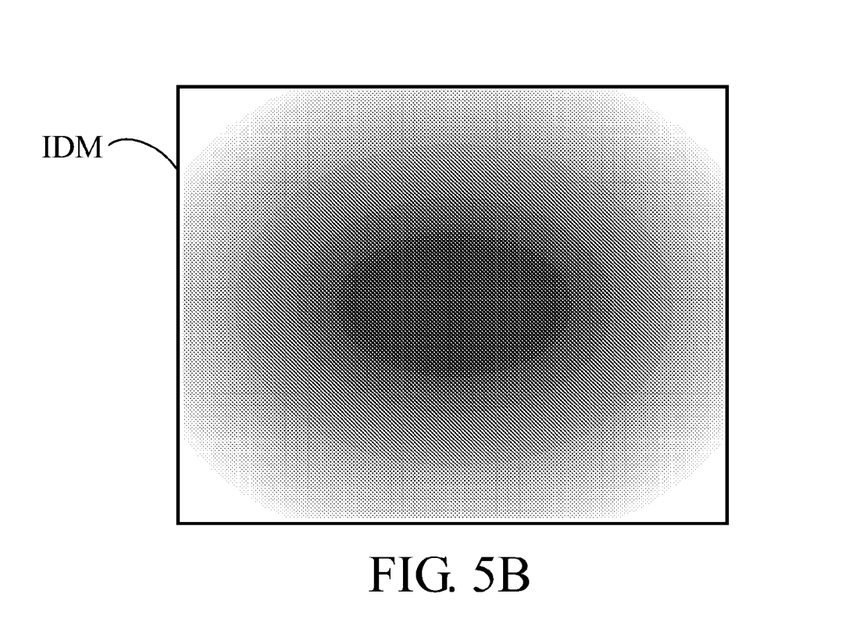
Figure 5C:
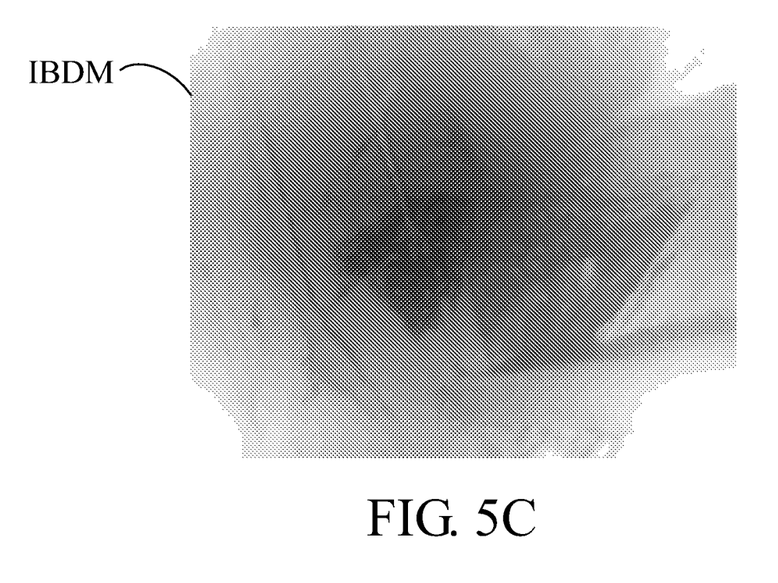

In step S2100, monoscopic images are obtained. Similarly, in some embodiments, the monoscopic images are obtained by capturing images of organs in an operating field, such as thorax, abdominal cavity, pelvic cavity, pericardial cavity, pleural cavity, and others via an endoscope. In step S2200, a background depth map of the operating field is calculated according to at least one monoscopic image. The background depth map of the operating field can be obtained in various manners. FIG. 3 is a flowchart of an exemplary embodiment of a method for calculating a background depth map of the disclosure. In step S2220, an initial background depth map corresponding to the operating field is obtained. It is noted that, the initial background depth map can be obtained in various manners. In some embodiments, a 2D to 3D conversion technique, such as the one disclosed in PCT/CN2009/075007 (A method of depth map creation from monocular video or image), can be applied to one key monoscopic image to obtain the initial background depth map. FIGS. 5A~5C show an example of an initial background depth map obtained by such a 2D to 3D conversion. An key monoscopic image KMI shown in FIG. 5A and an initial depth map IDM shown in FIG. 5B can be used to generate an initial background depth map IBDM corresponding to the operating field, as shown in FIG. 5C. It is understood that, such an initial background depth map can be further refined manually or semi-automatically off-line, and used online for a particular type of operation. In some embodiments, the distances from the organs to the endoscope can be measured by, for example, referring to data collected from previous operations, and the distances can be assigned as the initial background depth map. In some embodiments, the endoscope may be equipped with at least one sensor, and the distances from the organs to the endoscope can be detected using a depth from motion technique. For example, a position sensor can be set on the handle of the endoscope, such that the detected position in space and a derivative of the position can provide depth from movement. Further, in some embodiments, a scene model can be created using the collected data or captured by other medical imaging system such as Computed Tomography scans or Magnetic Resonance Imaging, and a 3D model of the scene is then the basis to obtain the initial background depth map. It is understood that, the above manners to obtain the initial background depth map are examples of the disclosure, and the disclosure is not limited thereto. In step S2222, the background depth maps are calculated according to the initial background depth map corresponding to one key monoscopic image and subsequent monoscopic images. It is understood that, in some embodiments, each of a plurality of pixels of the subsequent monoscopic image can be mapped to the initial background depth map according to positions of the pixels, in order to obtain corresponding initial depth values. Then, the initial depth values of each of the pixels of the subsequent monoscopic image are filtered using a cross-bilateral filter, in order to obtain depth information for each of the pixels in the background depth maps corresponding to each subsequent monoscopic images, such as described in the above mentioned disclosure PCT/CN2009/075007 (A method of depth map creation from monocular video or image). Another manner to obtain background depth map consist in propagating to subsequent images the initial background depth map obtained from one key monoscopic image, according to a method described for example in "Improved depth propagation for 2D to 3D video conversion using key-frames," C. Varekamp and B. Barenbrug, 4th European conference on Visual Media Production, 2007. IETCVMP, or other method of depth map propagation.

Figure 4:
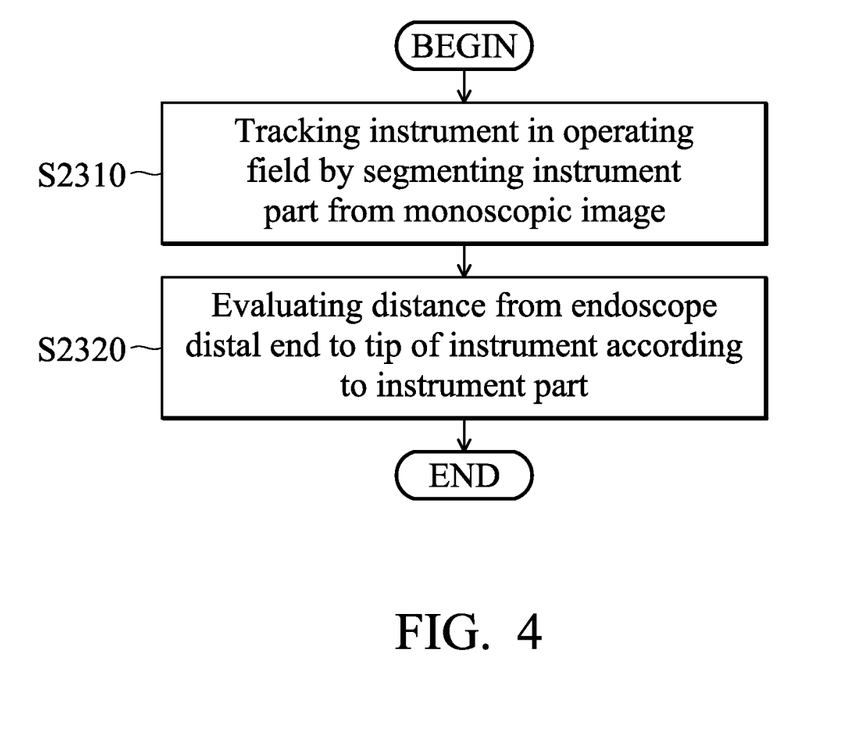
FIG. 4 is a flowchart of an exemplary embodiment of a method for calculating an instrument depth map of the disclosure.
Figure 6:
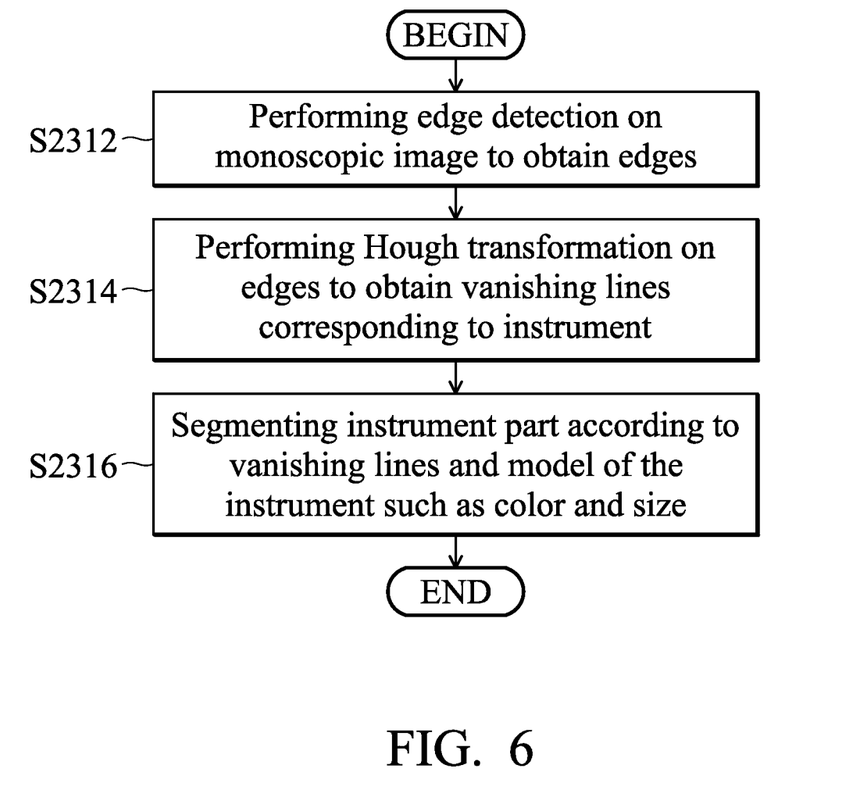
FIG. 6 is a flowchart of an exemplary embodiment of a method for segmenting the part of the instrument viewed in the field of view of the monoscopic images of the disclosure.
Figure 7:
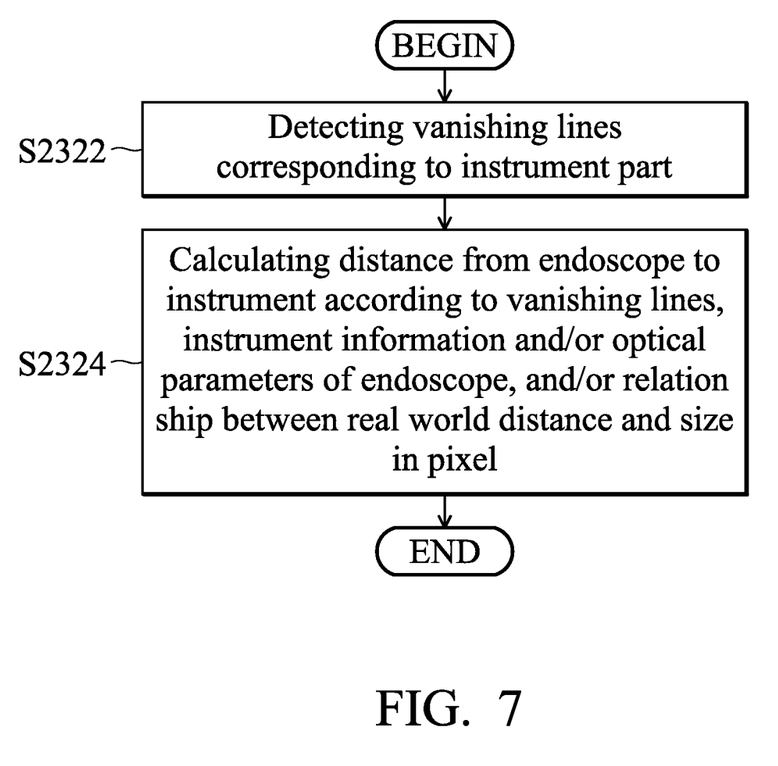
FIG. 7 is a flowchart of an exemplary embodiment of a method for evaluating a distance from an endoscope to an instrument of the disclosure.
Figure 8A:
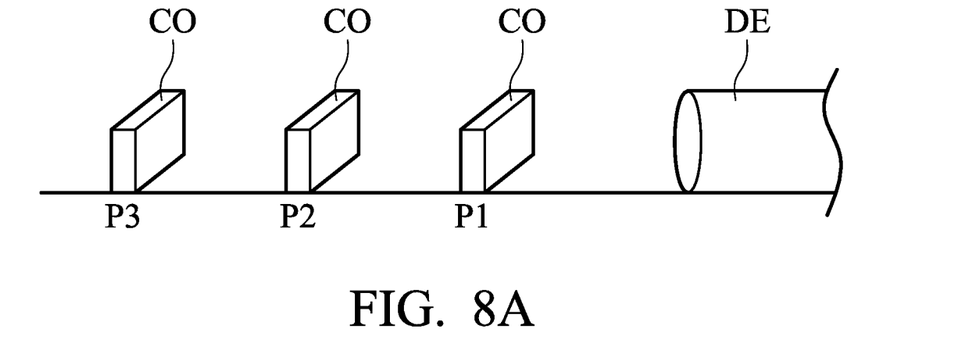
FIGS. 8A and 8B illustrate a calibration procedure for obtaining the relationship between distance and size of an object in pixels.
Figure 8B:
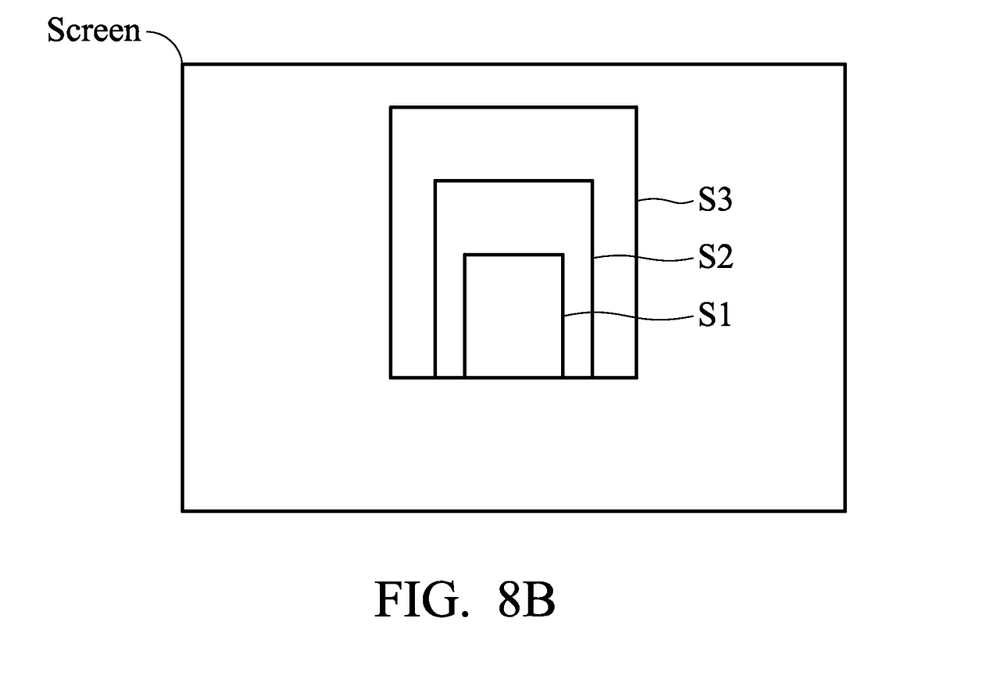

Referring to FIG. 2 again, in step S2300, an instrument depth map corresponding to one or more instrument, such as a grasper is calculated for each monoscopic image. As described, the instrument can be inserted in a patient's body cavity. FIG. 4 is a flowchart of an exemplary embodiment of a method for calculating an instrument depth map of the disclosure. First, in step S2310, the instrument in the operating field of an organ is tracked by segmenting an instrument part corresponding to the part of the instrument viewed in the field of view of the monoscopic image. FIG. 6 is a flowchart of an exemplary embodiment of a method for segmenting the part of the instrument viewed in the field of view of the monoscopic images of the disclosure. In step S2312, edge detection is performed on the monoscopic images to obtain edges in the monoscopic images. In step S2314, a Hough transformation is performed on the edges to obtain vanishing lines corresponding to the instrument. After the vanishing lines corresponding to the instrument are obtained, in step S2316, the instrument part is segmented from the monoscopic image according to the vanishing lines and model of the instrument, such as color and size. In some embodiments, the steps of FIG. 6 can be applied on the first or a limited number of images to segment the instrument part. Once the instrument part is obtained, edge detection can be performed on the following images, and the edges corresponding to the instrument part can be tracked to know the position of the instrument part. After the instrument part corresponding to the instrument is obtained, in step S2320 in FIG. 4, a distance from the endoscope distal end to the tip of the instrument is evaluated according to the instrument part. FIG. 7 is a flowchart of an exemplary embodiment of a method for evaluating a distance from an endoscope to an instrument of the disclosure. In step S2322, vanishing lines corresponding to the instrument part are detected. Then, in step S2324, the distance from the endoscope to the instrument, such as a distance from a distal end of the endoscope to a tip of the instrument is calculated according to the vanishing lines, instrument information and/or optical parameters of the endoscope, and/or relationship between real world distance and size in pixel. In some embodiments, a calibration is performed by measuring the size of a calibration object as seen on the screen and relating it to its distance from the distal end of the endoscope, such that a relationship between size of an object on the screen (measured for example in number of pixels) and its distance to the distal end of the endoscope is obtained. The FIGS. 8A and 8B illustrates this principle, with a calibration object CO of fixed size being positioned at different position (P1, P2 and P3) along a graduated rule, as shown in FIG. 8A. The calibration can be performed for different zoom ratio. It leads to at least one curve or a set of curve providing the relationship between the number of pixels on the screen and the distance from the distal end of the endoscope DE and the tip of the instrument. For example, the size of the calibration object CO positioned at different position (P1, P2 and P3) in the screen are different, as shown in FIG. 8B, in which S1 is the size in pixel at position P1, S2 is the size in pixel at position P2, and S3 is the size in pixel at position P3. The calibration described follows a preliminary step of camera image rectification in order to avoid image distortion, such as for example described in "Videoendoscopic distortion correction and its application to virtual guidance of endoscopy", IEEE Transact on Medical Imaging Volume: 20 Issue: 7. After the calibration process, the depth map corresponding to the instrument can be created by associating a grey level, for example from 0 to 255, to the depth found in the previous step. For example a grey level of 0 can be associated to the farthest distance from the distal end of the endoscope to the tip of the instrument, while a grey level of value of 255 can be associated to the closest distance from the distal end of the endoscope to the tip of the instrument. Also, the mapping between the actual depth of the grasper tip to the distal end of the endoscope can be linear or non-linear, following an appropriate relationship so that the depth is best rendered on the appropriate display.

Figure 9A:
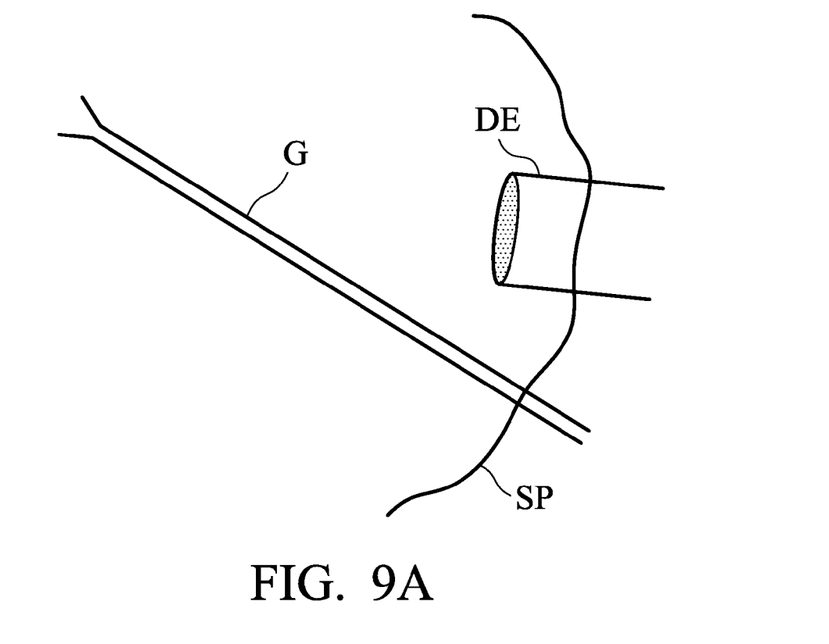
FIGS. 9A and 9B illustrate how to obtain distance of the tip of an instrument after detection of its vanishing lines and the step of calibration illustrated on FIGS. 8A and 8B.
Figure 9B:
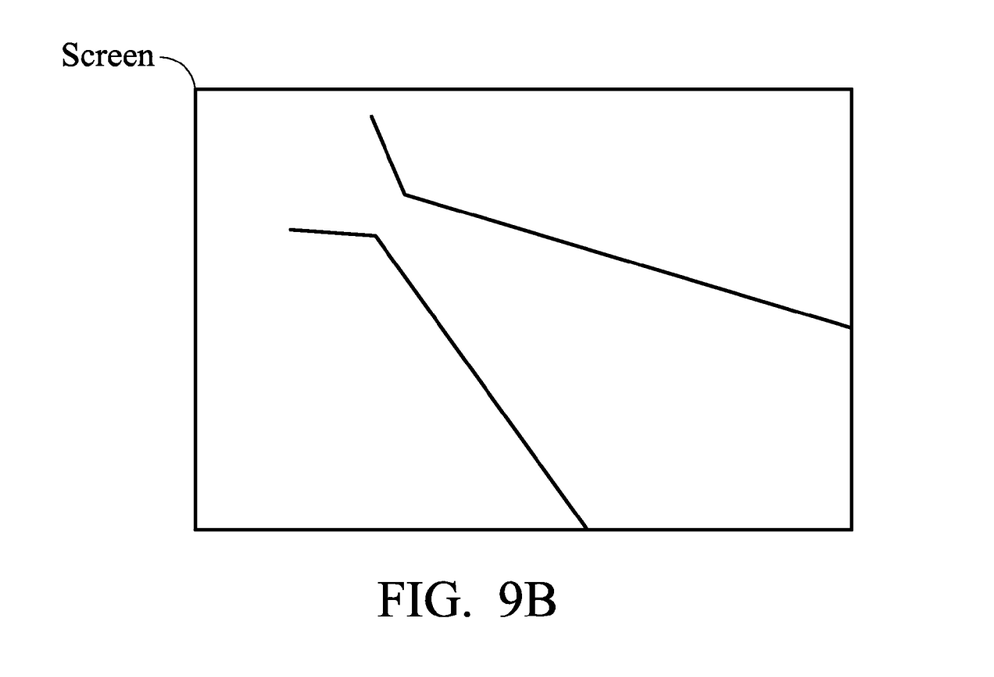
Figure 10A:
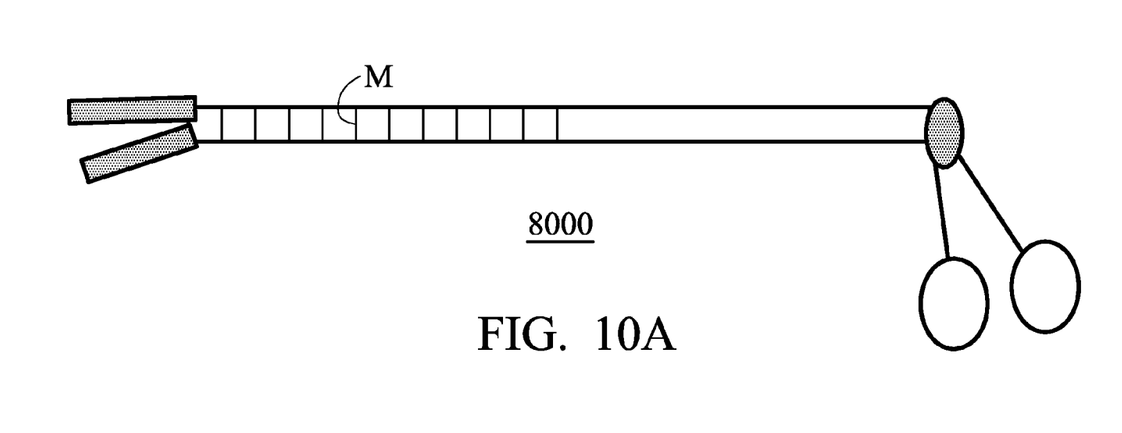
FIG. 10A is a schematic diagram illustrating an exemplary embodiment of an example of a grasper with markings of the disclosure.
Figure 10B:
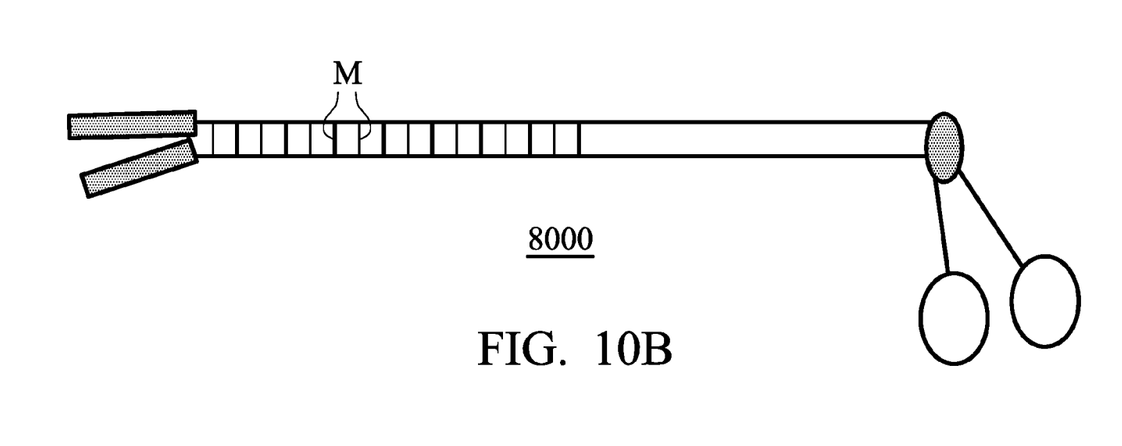
FIG. 10B is a schematic diagram illustrating another exemplary embodiment of an example of a grasper with markings of the disclosure.

As described, the distance from the endoscope to the instrument, such as a distance from a distal end of the endoscope to a tip of the instrument is calculated according to the vanishing lines, instrument information and/or optical parameters of the endoscope, and/or relationship between real world distance and size in pixel. FIGS. 9A and 9B illustrate how to obtain distance of the tip of an instrument after detection of its vanishing lines and the step of calibration illustrated on FIGS. 8A and 8B. As shown in FIG. 9A, a grasper G is inserted in the skin of the patient SP, and the endoscope DE captures an image corresponding to the grasper G in the field. The captured image is shown in the screen, as shown in FIG. 9B, in which the part of the grasper near to the lens of the endoscope appears bigger. The far distance dimension of the grasper can be measured (size in pixel), and the distance can be deduced. It is understood that the relationship between the number of pixels depends on the optical parameters of the endoscope. In some embodiments, the instrument may have instrument information, such as dimensions of the instrument, and/or characteristics, such as lines marked on the instrument. FIG. 10A is a schematic diagram illustrating an exemplary embodiment of an example of a grasper with markings of the disclosure. As shown in FIG. 10A, specific markings M with a known spacing (pitch) are imprinted or engraved on an instrument 8000. It is noted that the markings have to be on a long enough portion of the instrument so that they are a visible when the instrument is inserted in the body cavity of the patient. FIG. 10B is a schematic diagram illustrating another exemplary embodiment of an example of a grasper with markings of the disclosure. As shown in FIG. 10B, specific markings M with known dimensions (thickness) and spacing (pitch) are imprinted or engraved on an instrument 8000. Similarly, the markings have to be on a long enough portion of the instrument so that they are be at a visible when the instrument is inserted in the body cavity of the patient. The spacing of the markings are then used to calculate the depth of the instrument following the above calibration process and based on the described relationship between the number of pixels on the screen and the distance from the distal end of the endoscope to the tip of the instrument. It is understood that the distance from the endoscope to the instrument is then used to obtain the instrument depth map.

After the background depth map and the instrument depth map are obtained, for each monoscopic image, in step S2400, the background depth map and the instrument depth map are merged to generate an integrated depth map for each monoscopic image. It is understood that, in some embodiments, the background depth map and the instrument depth map can be normalized into a same scale, and the background depth map and the instrument depth map are merged in the same scale to generate the integrated depth map. In step S2500, stereoscopic views are generated according to the monoscopic images and the integrated depth map. It is understood that, in some embodiments, once the integrated depth map is obtained, at least two views, such as a right view and a left view can be generated in order to present a 3D view of the scene to the operator and other persons. Similarly, the display unit 1200 may be an autostereoscopic display, a parallax barrier or lenticular display, a head mount display, or a display with polarized glasses or time multiplexed glasses.

Therefore, the methods and systems of the present disclosure can generate stereoscopic views from monoscopic images captured by an endoscope. In the present disclosure, existing monoscopic endoscopes can be directly used without any hardware modification, thus reducing cost and size compared to classical approach of stereo endoscopes.

It is an objective of the present disclosure to provide an operator, such as a surgeon with depth impression when operating with an endoscope. Operations such as manipulating threads to sew organs, grasping organs and ablating organs are facilitated with the help of stereo vision.

Methods for generating stereoscopic views from monoscopic endoscope images, or certain aspects or portions thereof, may take the form of a program code (i.e., executable instructions) embodied in tangible media, such as floppy diskettes, CD-ROMS, hard drives, flash memories or any other machine-readable storage medium, wherein, when the program code is loaded into and executed by a machine, such as a computer, the machine thereby becomes an apparatus for practicing the methods. The methods may also be embodied in the form of a program code transmitted over some transmission medium, such as electrical wiring or cabling, through fiber optics, or via any other form of transmission, wherein, when the program code is received and loaded into and executed by a machine, such as a computer, the machine becomes an apparatus for practicing the disclosed methods. When implemented on a general purpose processor, the program code combines with the processor to provide a unique apparatus that operates analogously to application specific logic circuits. The disclosed method can also be implemented into a hardware device, of the Very Large Scale Integration (VLSI) type or of the Field Programmable Gate Array (FPGA) type, but are not limited to these types.

While the disclosure has been described by way of example and in terms of preferred exemplary embodiments, it is to be understood that the disclosure is not limited thereto. Those who are skilled in this technology can still make various alterations and modifications without departing from the scope and spirit of this disclosure. Therefore, the scope of the present disclosure shall be defined and protected by the following claims.

The invention claimed is:

1. A method for generating stereoscopic views from monoscopic endoscope images, comprises the following steps:
    obtaining monoscopic images, wherein the monoscopic images are obtained by capturing images of organs in an operating field via an endoscope;
    obtaining a background depth map of the operating field for each image;
    obtaining an instrument depth map corresponding to an instrument, wherein the instrument is inserted in a patient's body cavity for each image;

merging the background depth map and the instrument depth map to generate an integrated depth map for each image; and generating stereoscopic views according to the monoscopic images and the corresponding integrated depth maps.

2. The method of claim 1, wherein the step of obtaining the background depth maps is performed by first obtaining an initial background depth map from the operating field and a key monoscopic image and then propagating the initial background depth map to subsequent images.

3. The method of claim 2, wherein the initial background depth map is obtained by applying a 2D to 3D conversion technique to a key monoscopic image.

4. The method of claim 3, wherein the 2D to 3D conversion comprises the steps of:

mapping each of a plurality of pixels of the key monoscopic image to the initial background depth map according to positions of the pixels, in order to obtain corresponding initial depth values; and filtering the initial depth values of each of the pixels of the monoscopic image using a cross-bilateral filter, in order to obtain depth information for each of the pixels in the background depth map.

5. The method of claim 1, wherein the step of calculating the background depth maps is performed by a depth from motion technique, and can be assisted by the use of a position sensor placed on the endoscope.

6. The method of claim 1, wherein the step of calculating the instrument depth maps corresponding to the instrument as seen in each images comprises the steps of:

tracking the instrument in the operating field by segmenting the instrument part corresponding to the instrument seen in the monoscopic images; and evaluating a distance from the distal end of the endoscope to the instrument tip according to the instrument part, wherein the distance from the endoscope to the instrument is set as the instrument depth map.

7. The method of claim 6, wherein the step of segmenting the instrument part corresponding to the instrument seen in the monoscopic images comprises the steps of:

performing an edge detection on the monoscopic images to obtain edges in the monoscopic images;

performing a Hough transformation on the edges to obtain straight lines corresponding to the instrument; and segmenting the instrument part from the monoscopic images according to the edges corresponding to the instrument.

8. The method of claim 6, wherein the step of segmenting the instrument part corresponding to the instrument seen in the monoscopic images comprises the steps of:

performing an edge detection on the monoscopic images to obtain edges in the monoscopic images;

segmenting the instrument part from the monoscopic images according to the edges corresponding to the instrument and a model of the instrument, such as a color model or a size model or other characteristics of the instrument.

9. The method of claim 6, wherein the step of evaluating the distance from the endoscope to the instrument according to the instrument part comprises the steps of:

detecting vanishing lines corresponding to the instrument part; and calculating the distance from the endoscope to the instrument according to the vanishing lines, and the relationship between a distance on the visualization device in number of pixel and a distance from the distal end of the endoscope to the tip of the instrument.

10. The method of claim 8, wherein the relationship between a distance on the visualization device in number of pixel and a distance from the distal end of the endoscope to the tip of the instrument is found through a calibration consisting of first proceeding to the camera image rectification according to known computer vision camera image rectification techniques, second, positioning an object of known dimensions on a graduated scale; measuring the size in pixel of the object; and repeating the measurement for different position of the object on the graduated scale; the whole calibration can be repeated for different zoom levels, providing a set of calibration curves.

11. The method of claim 8, wherein the instrument information comprises dimensions of the instrument, or characteristics of the instrument, wherein the characteristics comprise lines marked or engraved on the instrument.

12. The method of claim 1, wherein the step of merging the background depth map and the instrument depth map to generate an integrated depth map comprises the steps of:

normalizing the background depth map and the instrument depth map into a same scale; and merging the background depth map and the instrument depth map in the same scale to generate the integrated depth map.

13. A system for generating stereoscopic views from monoscopic endoscope images, comprising:

a storage unit comprising monoscopic images, wherein the monoscopic images are obtained by capturing images of organs in an operating field via an endoscope; and a processing unit calculating a background depth map of the operating field, calculating an instrument depth map corresponding to an instrument, wherein the instrument is inserted in a patient's body cavity, merging the background depth map and the instrument depth map to generate an integrated depth map, and generating stereoscopic views according to the monoscopic images and the corresponding integrated depth maps.

14. The system of claim 13, wherein the processing unit calculates the background depth map by first obtaining an initial background depth map from the operating field and a key monoscopic image and then propagating the initial background depth map to subsequent images.

15. The system of claim 14, wherein the processing unit obtains the initial background depth map by applying a 2D to 3D conversion technique to a key monoscopic image.

16. The system of claim 15, wherein the processing unit applies the 2D to 3D conversion by mapping each of a plurality of pixels of the key monoscopic image to the initial background depth map according to positions of the pixels, in order to obtain corresponding initial depth values, and filtering the initial depth values of each of the pixels of the monoscopic images using a cross-bilateral filter, in order to obtain depth information for each of the pixels in the background depth map.

17. The system of claim 13, wherein the processing unit calculates the background depth map by a depth from motion technique, and can be assisted by the use of a position sensor placed on the endoscope.

18. The system of claim 13, wherein the processing unit calculates the instrument depth map corresponding to the instrument by tracking the instrument in the operating field by segmenting the instrument part corresponding to the instrument seen in the monoscopic images, and evaluating a distance from the distal end of the endoscope to the instrument tip according to the instrument part, wherein the distance from the endoscope to the instrument is set as the instrument depth map.

19. The system of claim 18, wherein the processing unit segments the instrument part corresponding to the instrument seen in the monoscopic images by performing an edge detection on the monoscopic images to obtain edges in the monoscopic images, performing a Hough transformation on the edges to obtain straight lines corresponding to the instrument, and segmenting the instrument part from the monoscopic images according to the edges corresponding to the instrument.

20. The system of claim 18, wherein the processing unit segments the instrument part corresponding to the instrument seen in the monoscopic images by performing an edge detection on the monoscopic images to obtain edges in the monoscopic images, and segmenting the instrument part from the monoscopic images according to the edges corresponding to the instrument and a model of the instrument, such as a color model or a size model.

21. The system of claim 18, wherein the processing unit evaluates the distance from the endoscope to the instrument according to the instrument part by detecting vanishing lines corresponding to the instrument part, and calculating the distance from the endoscope to the instrument according to the vanishing lines, and the relationship between a distance on the visualization device in number of pixel and a distance from the distal end of the endoscope to the tip of the instrument.

22. The system of claim 20, wherein the relationship providing the relationship between a distance on the visualization device in number of pixel and a distance from a distal end of the endoscope to a tip of the instrument is found through a calibration consisting of first proceeding to the camera image rectification according to known computer vision camera image rectification techniques, second, positioning an object of known dimensions on a graduated scale; measuring the size in pixel of the object; and repeating the measurement for different position of the object on the graduated scale; the whole calibration can be repeated for different zoom level, providing a set of calibration curves.

23. The system of claim 20, wherein the instrument information comprises dimensions of the instrument, or characteristics of the instrument, wherein the characteristics comprise lines marked or engraved on the instrument.

24. The system of claim 13, wherein the processing unit merges the background depth map and the instrument depth map to generate an integrated depth map by normalizing the background depth map and the instrument depth map into a same scale, and merging the background depth map and the instrument depth map in the same scale to generate the integrated depth map.

25. A non-transitory machine-readable storage medium comprising a computer program, which, when executed, causes a device to perform a method for generating stereoscopic views from monoscopic endoscope images, wherein the method comprises:
  obtaining monoscopic images, wherein the monoscopic images are obtained by capturing images of organs in an operating field via an endoscope,
  obtaining a background depth map of the operating field for each image;
  obtaining an instrument depth map corresponding to an instrument, wherein the instrument is inserted in a patient's body cavity for each image;
  merging the background depth map and the instrument depth map to generate an integrated depth map for each image; and
  generating stereoscopic views according to the monoscopic images and the corresponding integrated depth maps.

* * * * *